(12) United States Patent
Kline et al.

(10) Patent No.: US 7,737,298 B2
(45) Date of Patent: Jun. 15, 2010

(54) PRODUCTION OF ACETIC ACID AND MIXTURES OF ACETIC ACID AND ACETIC ANHYDRIDE

(75) Inventors: Robert Sterling Kline, Johnson City, TN (US); Gregory Abbott Wellman, Jr., Kingsport, TN (US); Brandon Tyler Earls, Kingsport, TN (US); Jerry Lee Bewley, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 224 days.

(21) Appl. No.: 11/423,383

(22) Filed: Jun. 9, 2006

(65) Prior Publication Data
US 2007/0287862 A1    Dec. 13, 2007

(51) Int. Cl.
C07C 51/12    (2006.01)

(52) U.S. Cl. .................. 562/519; 562/517; 562/890; 562/891

(58) Field of Classification Search .................. 562/519, 562/517, 890, 891
See application file for complete search history.

(56) References Cited

U.S. PATENT DOCUMENTS

| | | | |
|---|---|---|---|
| 3,772,380 A | 11/1973 | Paulik et al | |
| 3,927,078 A | 12/1975 | Lapporte et al | |
| 4,046,807 A | 9/1977 | Kuckertz | |
| 4,115,444 A | 9/1978 | Rizkalla | |
| 4,252,741 A | 2/1981 | Porcelli et al. | |
| 4,333,884 A | 6/1982 | Kubbeler et al. | |
| 4,358,411 A | 11/1982 | Porcelli et al. | |
| 4,366,259 A | 12/1982 | Knifton et al. | |
| 4,374,070 A | 2/1983 | Larkins et al. | |
| 4,417,077 A | 11/1983 | Drago et al. | |
| 4,430,273 A | 2/1984 | Erpenbach et al. | |
| 4,559,183 A | 12/1985 | Hewlitt | |
| 4,629,809 A | 12/1986 | Vanderpool et al. | |
| 5,003,104 A | 3/1991 | Paulik et al. | |
| 5,144,068 A | 9/1992 | Smith et al. | |
| 5,258,549 A | 11/1993 | Pimblett | |
| 5,292,948 A | 3/1994 | Zoeller et al. | |
| 5,298,586 A | 3/1994 | Beevor et al. | |
| 5,380,929 A * | 1/1995 | Erpenbach et al. | 562/519 |
| 5,416,237 A | 5/1995 | Aubigne et al. | |
| 5,442,107 A | 8/1995 | Beevor et al. | |
| 5,488,143 A | 1/1996 | Uhm et al. | |
| 5,510,524 A | 4/1996 | Garland et al. | |
| 5,648,531 A * | 7/1997 | Morimoto et al. | 562/891 |
| 5,900,505 A | 5/1999 | Tustin et al. | |
| 5,922,911 A | 7/1999 | Jones et al. | |
| 6,130,355 A | 10/2000 | Jones | |
| 6,211,405 B1 | 4/2001 | Cheung et al. | |
| 6,452,043 B1 | 9/2002 | Zoeller et al. | |
| 6,667,418 B2 | 12/2003 | Broussard et al. | |
| 6,916,951 B2 | 7/2005 | Tustin et al. | |
| 7,115,774 B2 | 10/2006 | Magna et al. | |

FOREIGN PATENT DOCUMENTS

| | | |
|---|---|---|
| EP | 0008396 A1 | 5/1980 |
| EP | 0081152 A | 6/1983 |
| EP | 0109212 A | 5/1984 |
| EP | 0087870 B1 | 4/1985 |
| EP | 0096974 B1 | 9/1985 |
| EP | 0153834 | 9/1985 |
| EP | 0087869 B1 | 7/1986 |
| EP | 0338730 A1 | 10/1989 |
| EP | 0391680 | 10/1990 |
| EP | 0584964 | 3/1994 |
| EP | 0752406 | 1/1997 |
| EP | 0976711 A1 | 2/2000 |
| GB | 1 234 641 A | 6/1971 |
| GB | 2029409 | 3/1980 |
| JP | 146933 A | 5/2003 |
| WO | 99/54273 A1 | 10/1999 |

OTHER PUBLICATIONS

International Search Report and Accompanying Written Opinion issued in related International Patent Application No. PCT/US2007/012457 on Dec. 19, 2007.

Howard et al, Catalysis Today, 18, (1993) pp. 325-354.

W. Bertleff, Carbonylation, Ulmann's Encyclopedia of Industrial Chemistry, 6th Edition, vol. 6, Wiley-VCH Verlag GmbH & Co. KGaA, Weinheim, Germany, p. 473 (2003).

(Continued)

*Primary Examiner*—Daniel M Sullivan
*Assistant Examiner*—Sudhakar Katakam
(74) *Attorney, Agent, or Firm*—Eric D. Middlemas; Bernard J. Graves, Jr.

(57) ABSTRACT

Disclosed is a process for the production of acetic acid or mixtures of acetic acid and acetic anhydride in a carbonylation process wherein a mixture comprising methyl acetate and/or dimethyl ether and methyl iodide is contacting in the liquid phase with carbon monoxide in the presence of a carbonylation catalyst at elevated pressures and temperatures. Methanol, water, or a mixture thereof is added to an acetic anhydride-containing stream within a flash evaporation zone to convert some or all of the acetic anhydride to acetic acid and optionally methyl acetate and to provide heat for the evaporation of a portion of the product effluent produced by the carbonylation process.

14 Claims, 3 Drawing Sheets

OTHER PUBLICATIONS

W. Rienmenschneider, "Carboxylic Acids, Aliphatic", Ulmann's Encyclopedia of Industrial Chemistry, 6th Edition, vol. 6, Wiley-VCH Verlag GmbH & Co. KGaA, Weinheim, Germany, p. 493 (2003).

Yoneda, et al, "Recent Advances in processes and catalysts for the production of acetic acid", Applied Catalysis A: General 221 (2001) 253-265.

De Blasio et al, "Activity and Stability of Two Polymer-Supported Rhodium-Based Catalysts for the Vapour Phase Carbonylation of Methanol", Journal of Catalysis, 176, (1998) 253-259.

Sunley, et al, "High productivity methanol carbonylation catalysis using iridium The Cativa (TM) process for the manufacture of acetic acid", Catalysis Today, 58 (2000) 293-307.

* cited by examiner

PRODUCTION OF ACETIC ACID AND MIXTURES OF ACETIC ACID AND ACETIC ANHYDRIDE

FIELD OF THE INVENTION

This invention pertains to a process for the production of acetic acid or a mixture of acetic acid and acetic anhydride by contacting an acetic anhydride-containing stream with methanol, water, or a mixture thereof to convert some or all of the acetic anhydride to acetic acid and methyl acetate. More specifically, the present invention pertains to the addition of methanol and/or water to an acetic anhydride-containing stream within a flash evaporation zone to convert some or all of the acetic anhydride to acetic acid and methyl acetate and to provide heat for the evaporation of a portion of a product effluent produced by contacting a mixture comprising methyl acetate and/or dimethyl ether and methyl iodide with carbon monoxide in the presence of a carbonylation catalyst.

BACKGROUND OF THE INVENTION

The preparation of acetic anhydride by contacting in the liquid phase a mixture comprising methyl acetate and/or dimethyl ether and methyl iodide with carbon monoxide in the presence of a carbonylation catalyst at elevated pressures and temperatures has been reported extensively in the patent literature. See, for example, U.S. Pat. Nos. 3,927,078; 4,046,807; 4,115,444; 4,252,741; 4,374,070; 4,430,273; 4,559,183; 5,003,104; 5,292,948 and 5,922,911 and European Patents 8396; 87,869; and 87,870. These patents disclose that the reaction rate can be increased if the catalyst system includes a promoter such as certain amines and quaternary ammonium compounds, phosphines and phosphonium compounds and inorganic compounds such as alkali metal salts e.g., lithium iodide. Normally, both the reaction (process) mixture and the crude product are substantially anhydrous, homogeneous liquids comprising a solution of the reactants and catalyst components in an inert solvent such as acetic acid. Thus, the crude, liquid product obtained from such acetic anhydride processes typically comprises a mixture of acetic anhydride and acetic acid as a result of the use of acetic acid as a process solvent.

Acetic acid may be coproduced in the process by feeding methanol and/or water to the production system, e.g., by feeding methanol and/or water to a process recycle stream containing acetic anhydride and/or to the carbonylation reactor. See, for example, U.S. Pat. Nos. 5,380,929, 6,130,355, EP-00087869-B1 and EP-00087870-B1. U.S. Pat. No. 4,374,070 discloses the possibility of adding methanol to an acetic anhydride-containing recycle stream.

The above-described processes for the manufacture of acetic anhydride are carried out by feeding carbon monoxide to a reaction zone containing a liquid mixture of (i) a feedstock compound selected from methyl acetate, dimethyl ether or a mixture thereof, (ii) methyl iodide and (iii) a carbonylation catalyst such as a Group VIII metal or metal compound and, optionally, one or more promoters. The carbon monoxide typically is fed below the surface of the liquid mixture in a finely divided form, e.g., by means of a gas sparging device, to maximize the concentration of carbon monoxide in the reaction mixture. Normally, the process is operated by feeding continuously the feedstock compound(s), methyl iodide, an inert solvent such as acetic acid, and catalyst or catalyst components dissolved in acetic anhydride and/or acetic acid and carbon monoxide to a reaction zone maintained at elevated temperature and pressure and removing continuously from the reaction zone a crude product mixture comprising acetic anhydride and acetic acid. The crude product mixture also contains feedstock compound(s), methyl iodide, acetic acid solvent, ethylidene diacetate, acetone, catalyst components and carbon monoxide dissolved in the crude product.

The crude product typically is fed continuously to a first separation zone wherein the pressure is reduced and the crude product flash distilled to produce (i) a vapor effluent comprising feedstock compound, methyl iodide, acetic acid solvent or product, acetic anhydride product, small amounts of by-product ethylidene diacetate and acetone and carbon monoxide and (ii) a liquid effluent comprising the catalyst or catalyst components dissolved in a mixture of acetic anhydride, acetic acid and small amounts of low boilers, e.g., feedstock compound, methyl iodide and acetone. The vapor effluent typically comprises about 20 to 60 weight percent of the crude product fed to the first separation zone. The liquid effluent is recycled to the reaction zone and the vapor effluent is fed to a product recovery zone wherein the acetic anhydride (and any coproduced acetic acid) is separated and removed from the production system. The other condensable components (methyl acetate, methyl iodide and acetic acid solvent) typically are recovered and recycled to the reaction zone. Co-product acetic acid may be recovered and removed from the process.

In the co-production of acetic acid and acetic anhydride, e.g., as described in U.S. Pat. Nos. 5,380,929 and 6,130,355, methanol and methyl acetate are fed to the primary carbonylation reactor and the products are produced in the presence of CO in a one-step reaction. In such processes, all of the heat of reaction is released in the single reaction step and there is no opportunity to utilize the heat of reaction directly in the production system such as in subsequent flash evaporation or distillation steps. The heat of reaction for methanol carbonylation is quite high, e.g., about twice that of the heat of reaction for methyl acetate carbonylation. Thus, a large amount of heat must be removed from the primary carbonylation reactor under severe conditions of high pressure and a corrosive environment. Furthermore, there is no opportunity to sequence the reactions in such a way as to obtain a beneficial shifting of reaction equilibrium.

BRIEF SUMMARY OF THE INVENTION

We have developed a process for the production of acetic acid or a mixture of acetic acid and acetic anhydride by the addition of methanol, water, or a mixture thereof to an acetic anhydride-containing stream within a flash evaporation zone wherein some or all of the acetic anhydride is converted to acetic acid or acetic acid and methyl acetate and the heat of the acetic anhydride/methanol and/or acetic anhydride/water reaction is utilized in the evaporation of the acetic acid/acetic anhydride product or the acetic acid product. The present invention thus provides a process for the co-production of acetic anhydride and/or acetic acid in the liquid phase under substantially anhydrous conditions which comprises the steps of:

(1) continuously feeding to a reaction zone (i) a feedstock compound selected from methyl acetate, dimethyl ether or a mixture thereof, (ii) methyl iodide, (iii) dissolved catalyst components, (iv) acetic acid, and (v) carbon monoxide, wherein the feedstock compound is converted to acetic anhydride at a temperature of about 100 to 300° C. and a pressure (total) of about 21 to 276 bar gauge (barg) to produce a liquid reaction mixture comprising (i) a feedstock compound selected from methyl acetate, dimethyl ether or a mixture thereof, (ii) methyl iodide, (iii) dissolved catalyst components, (iv) acetic acid, (v) dissolved carbon monoxide and (vi) acetic anhydride product;

(2) feeding a liquid carbonylation product effluent from the reaction zone to an evaporation zone comprising at least one evaporation vessel wherein the pressure (total) is about 1 to 10 barg;

(3) removing from the evaporation zone a vapor product effluent constituting about 30 to 90 weight percent of the liquid reaction mixture fed to the evaporation zone and comprising the feedstock compound, methyl iodide, acetic acid, and, optionally, acetic anhydride; and (4) removing from the evaporation zone a liquid product effluent constituting about 10 to 70 weight percent of the liquid reaction mixture fed to the evaporation zone and comprising acetic acid, dissolved catalyst components, and, optionally, acetic anhydride;

wherein methanol, water or a mixture thereof is combined with liquid carbonylation product effluent (i) fed to the evaporation zone and/or (ii) within the evaporation zone and reacts exothermically with acetic anhydride to produce acetic acid or a mixture of acetic acid and methyl acetate and the heat of the methanol/acetic anhydride and/or water/acetic anhydride reaction increases the weight percent of vapor product removed from the evaporation zone.

BRIEF DESCRIPTION OF THE DRAWING

The accompanying FIG. 1 is process flow diagram depicting one embodiment of the present invention in which methanol, water, or a mixture thereof is fed to a reduced pressure product stream and the resulting mixture is fed to an evaporation vessel. FIG. 2 is a process flow diagram depicting another embodiment of the invention in which a reduced pressure product stream is fed to a first evaporation vessel wherein a portion of the liquid feed is vaporized adiabatically and the liquid residue (material not vaporized) is transferred to a second evaporation vessel via a conduit to which methanol and/or water is added. FIG. 3 is a process flow diagram depicting a variation of the process represented by FIG. 2, in which the liquid residue from the second evaporation vessel is heated and fed to a third evaporation vessel wherein additional material is vaporized. While the invention is susceptible to embodiment in various forms, there is shown in the accompanying FIGS. 1, 2, and 3 and hereinafter in detail preferred embodiments of the invention.

DETAILED DESCRIPTION

Figure 1:
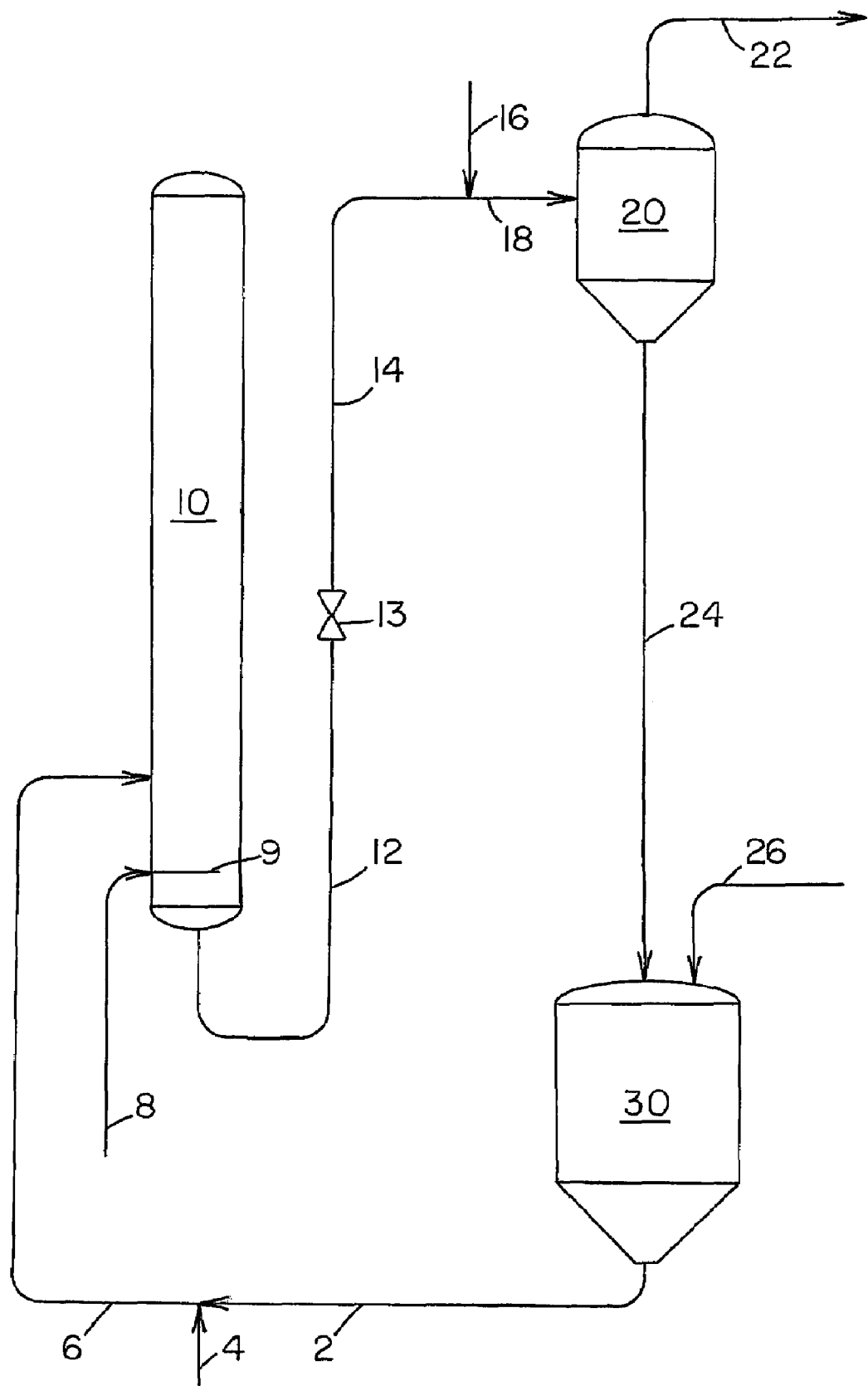
FIGS. 1-3 are process flow diagrams illustrating a system embodying the principles of the present invention.

The present invention is employed in conjunction with a production system for the manufacture, purification and recovery of acetic acid or a mixture of acetic anhydride and acetic acid. The synthesis or carbonylation section of the production system comprises feeding to a reaction zone (i) a feedstock compound selected from methyl acetate, dimethyl ether or a mixture thereof, (ii) methyl iodide, (iii) dissolved catalyst or catalyst components, (iv) acetic acid, and (v) carbon monoxide. The feedstock compound is converted to acetic anhydride at a temperature of about 100 to 300° C. and a pressure (total) of about 21 to 276 bar gauge (barg) to produce a liquid reaction mixture comprising (i) a feedstock compound selected from methyl acetate, dimethyl ether or a mixture thereof, (ii) methyl iodide, (iii) dissolved catalyst components, (iv) acetic acid, (v) dissolved carbon monoxide and (vi) acetic anhydride product. The liquid reaction mixture usually also contains small concentrations of acetone, ethylidene diacetate, acetyl iodide and other by- or co-products. Some or all of the carbonylation section of the process of the present invention is operated under substantially anhydrous conditions, i.e., under steady state operating conditions water either cannot be detected or can be detected only in trace amounts. Any water fed to the carbonylation section of the process normally is consumed by acetic anhydride present. The feed to the reaction zone typically comprise about 30 to 80 weight percent feedstock compound, about 5 to 20 weight percent methyl iodide, and about 5 to 30 weight percent acetic acid. The feed also may contain up to about 10 weight percent acetic anhydride as a component of a recycle catalyst stream. The mole ratio of feedstock compound to methyl iodide typically is in the range of about 4:1 to 10:1.

The reaction zone may comprise one or more pressure vessels which may be provided with means for agitation. The vessel design may be a pipe reactor, column, tank, stirred tank or other design. It is preferred that the reaction zone comprises at least one generally columnar vessel equipped with one or more internal baffles which, in combination with the carbon monoxide gas sparger feed device, create a highly agitated, recirculating reaction mixture. The residence time of the reactant within the first reaction zone normally is at least 20 minutes and, preferably, is in the range of about 30 to 50 minutes.

The feedstock compound(s), methyl iodide and carbon monoxide, react in the reaction zone to form acetic anhydride to produce a liquid reaction mixture comprising (i) a reactant compound selected from methyl acetate, dimethyl ether or a mixture thereof, (ii) methyl iodide, (iii) dissolved catalyst or catalyst components, typically a Group VIII metal or metal compound and one or more promoters, (iv) acetic acid, (v) dissolved carbon monoxide and (vi) acetic anhydride product. The reaction zone preferably is maintained at a temperature and pressure (total) of about 175 to 220° C. and 37 to 106 barg. The gas fed to the carbonylation zone may consist of essentially carbon monoxide or a mixture of carbon monoxide and hydrogen, e.g., a mixture of carbon monoxide and up to 7 volume percent hydrogen.

The carbonylation catalyst employed in the reaction zone may be any catalyst known to promote the reaction of carbon monoxide with the feedstock and methyl iodide. The catalyst typically is a Group VIII metal or metal compound such as a noble metal or noble metal compound. The catalyst preferably is rhodium, iridium or a compound thereof, most preferably a rhodium compound. The catalyst system may be provided to the process in various forms such as salts, e.g., rhodium trichloride or triiodide, rhodium hydrate, or rhodium carbonyl complexes, e.g., $[Rh(CO)_2I]_2$ from which the soluble, catalytically-active complex is formed. See, for example, the catalyst description in U.S. Pat. No. 4,374,070 and Roth et al., Chem. Tech., 1971 p. 600. The concentration of the catalyst metal in the liquid mixtures contained in the reaction zones normally is from abut 250 to 1300 ppm, although concentrations of 400 to 1000 ppm typically are used.

The promoter component of the catalyst system may be (1) an inorganic iodide salt such as lithium iodide or an iodide salt of a quaternary organophosphorus or organonitrogen compound or (2) an inorganic compound or an organophosphorus or organonitrogen compound which forms an iodide salt in the carbonylation zone. The organophosphorus or organonitrogen iodides may be selected from phosphonium iodides, ammonium iodides and heterocyclic aromatic compounds in which at least one ring hetero atom is a quaternary nitrogen atom. Examples of such phosphorus- and nitrogen-containing iodides include tetra(hydrocarbyl)phosphonium iodides such as tributyl(methyl)phosphonium iodide, tetrabutylphosphonium iodide, tetraoctylphosphonium iodide, triphenyl(methyl)phosphonium iodide, tetraphenylphosphonium iodide and the like; tetra(hydrocarbyl)ammonium iodides such as tetrabutylammonium iodide and tributyl(methyl)ammonium iodide; and heterocyclic aromatic compounds such as N-methylpyridinium iodide, N,N'-dimethylimidazolium iodide, N-methyl-3-picolinium iodide, N-methyl-2,4-litidinium iodide, N-methyl-2,4-lutidinium iodide and N-methylquinolinium iodide. The preferred iodide salt promoters comprise alkali metal iodide, e.g, lithium and sodium iodide, and tetraalkylphosphonium iodides, triphenyl(alkyl)phosphonium iodides, tetraalkylammonium iodides and N,N'-dialkylimidazolium iodides wherein the alkyl groups contain up to 8 carbon atoms.

A portion or all of the promoter compound may be fed as a compound which forms an iodide salt in the carbonylation zone. Thus, the promoter compounds may be fed initially in the form of their corresponding acetates, hydroxides, chlorides or bromides or the phosphorus- and nitrogen-containing promoters may be fed as compounds in which the phosphorus or nitrogen atoms are trivalent, e.g., tributylphosphine, tributylamine, pyridine, imidazole, N-methylimidazole and the like, which are quaternized by the methyl iodide present in the carbonylation zone.

The amount of the iodide compound promoter present in the carbonylation zone can be varied substantially depending on a variety of factors, especially on the particular promoter used. For example, the concentration of lithium iodide in the reaction mixture may range from 175 to 5000 ppm Li, preferably 1500 to 3700 ppm Li, whereas the phosphorus- and nitrogen-containing promoters may be present in concentrations of 0.5 to 25 weight percent, calculated as their iodide salts and based on the total weight of the reaction mixture, i.e., the contents of the carbonylation zone. The amounts of other materials, e.g., acetic acid, acetic anhydride, methyl iodide, methyl acetate and/or dimethyl ether present in the reaction mixture vary substantially depending, for example, on the carbonylation rate, residence time and concentrations of the iodide salt promoter and acetic acid solvent.

A liquid carbonylation product effluent is removed from the carbonylation zone and fed to an evaporation zone wherein the liquid product is separated into a vapor fraction and a liquid fraction. The liquid carbonylation product effluent may comprise about 15 to 50 weight percent acetic anhydride, about 5 to 60 weight percent acetic acid, about 15 to 40 weight percent feedstock compound, about 5 to 20 weight percent methyl iodide, dissolved catalyst or catalyst components, and small amounts of acetone, ethylidene diacetate, acetyl iodide and process tars. The vapor fraction comprises acetic acid and low boiling components such as methyl iodide, methyl acetate and/or dimethyl ether. The vapor fraction also may contain acetic anhydride not converted to acetic acid, methyl acetate or a mixture thereof by methanol and/or water addition. The vapor fraction also contains minor amounts of by-products such as ethylidene diacetate, acetone, acetyl iodide, etc. The vapor fraction preferably comprises up to about 40 weight percent acetic anhydride, about 15 to 50 weight percent acetic acid, about 30 to 55 weight percent low boiling components, and about 1 to 6 weight percent by-products/co-products. The liquid fraction comprises a solution of catalyst or catalyst components in acetic acid or a mixture of acetic acid and acetic anhydride. The liquid fraction typically is recycled to the carbonylation zone and the vapor fraction is separated into its component parts by a series of distillations.

The initial separation of the liquid carbonylation product effluent (product) into vapor and liquid fractions is carried in an evaporation zone wherein the pressure of the product is reduced to about 1 to 10 barg and partial vaporization occurs in one or more evaporation vessels. The amount of material vaporized (depth of flash) may be increased by providing additional heat to the liquid product feed stream to the to a flash evaporation vessel. In accordance with the present invention, some or all of the additional heat required for increasing the depth of flash is provided by contacting the liquid product feed with methanol to cause an exothermic reaction of the methanol and/or water with acetic anhydride present in the product stream. The methanol and/or water addition also increases the acetic acid produced by the carbonylation process. The total amount of methanol and/or water added to the liquid carbonylation product effluent can vary substantially depending on the amounts of acetic acid and/or acetic anhydride and acetic acid that are desired. For example, the total amount of methanol and/or added can vary from about 0.1 to 1 mole of methanol and/or water per mole of acetic anhydride present in the product stream. In a preferred embodiment, about 0.3 to 0.6 mole, of methanol is added per mole of acetic anhydride present in the product stream. The point at which the exothermic reaction occurs within the evaporation zone depends on the particular equipment (and the arrangement thereof) constituting the evaporation zone. In one embodiment of the present invention (as depicted by FIG. 1), methanol, water, or a mixture thereof is fed to a reduced pressure product stream and the resulting mixture is fed to an evaporation vessel. Depending upon variables such as the temperature of the product effluent from the carbonylation zone, the reduced pressure within the evaporation zone and the amount of methanol and/or water added, the depth of flash, i.e., the weight percent of material vaporized, achievable using such a single evaporation vessel may vary from about 30 to 80%. The product vapor is fed to a refining system wherein low boilers are recovered for recycle to the carbonylation zone and acetic acid and, optionally, acetic anhydride are separated and recovered.

Figure 2:
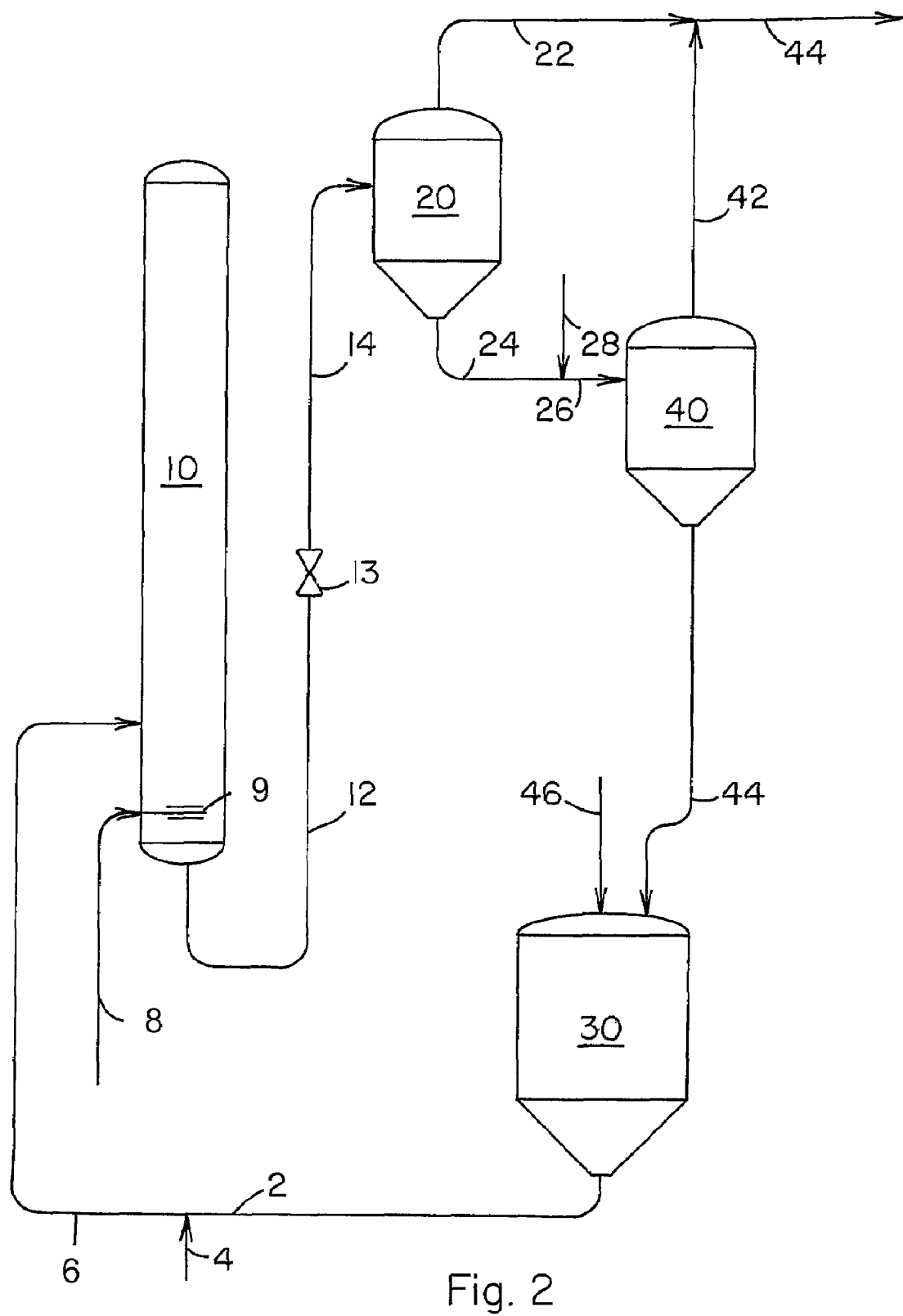
Figure 3:
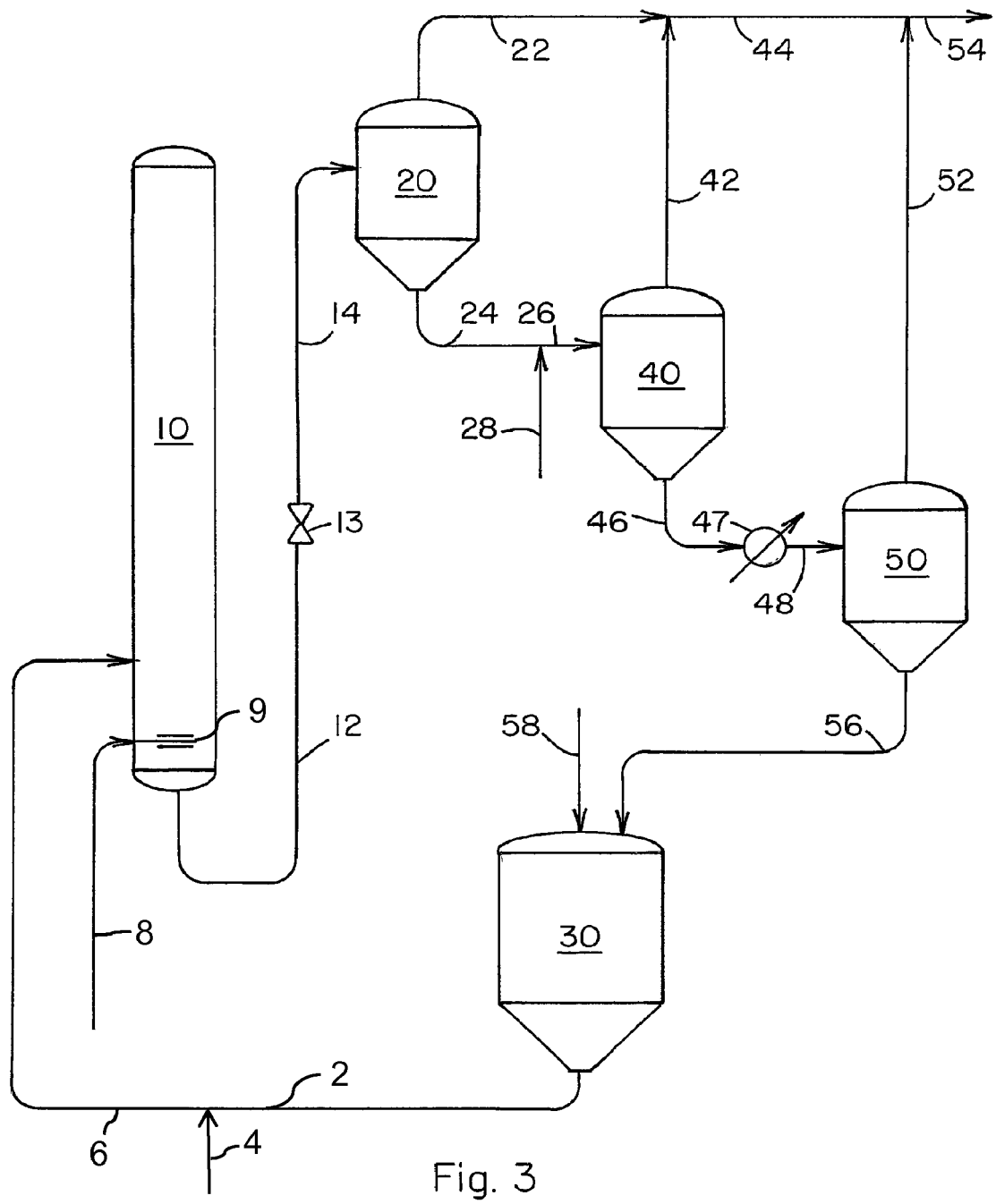

In a second embodiment of the present invention (as depicted by FIG. 2), a reduced pressure product stream is fed to a first evaporation vessel wherein a portion of the liquid feed is vaporized adiabatically and the liquid residue (material not vaporized) is transferred to a second evaporation vessel via a conduit to which methanol and/or water is added. The heat generated by the methanol/acetic anhydride and/or water/acetic anhydride reaction causes additional material to be vaporized. Depending upon the variables mentioned above, the total depth of flash achievable according to this second embodiment employing two evaporation vessels may vary from about 30 to 80%. A third embodiment of the present invention (as depicted by FIG. 3), is similar to the second embodiment except that the liquid residue from the second evaporation vessel is heated, e.g., by means of a heat exchanger, and fed to a third evaporation vessel wherein additional material is vaporized. Depending upon the variables mentioned above plus the extent to which the liquid residue from the second evaporation vessel is heated, the depth of flash achievable according to this third embodiment employing three evaporation vessels may vary from about 30 to 90%.

Referring to accompanying FIG. 1, a liquid carbonylation product effluent is removed from carbonylation reactor 10 by conduit 12 and passed through pressure reduction valve 13.

The reduced pressure carbonylation product is transferred to evaporation vessel 20 by conduits 14 and 18. Methanol, water, or a mixture thereof is fed via conduit 16 to conduit 14 wherein the methanol reacts exothermically with acetic anhydride to produce acetic acid or a mixture of acetic acid and methyl acetate. The heat generated by the methanol and/or water addition assists in the vaporization of about 30 to 80 weight percent of the material fed to evaporator 20. The vapor comprising acetic acid, optionally acetic anhydride and low boilers such as methyl acetate, carbon monoxide, and methyl iodide is removed from evaporator 20 and transferred to a product separation and recovery zone (not shown) by conduit 22. The liquid residue comprising acetic acid, optionally acetic anhydride and catalyst or catalyst components is removed from evaporator 20 by conduit 24 and fed to catalyst recycle tank 30. Materials required for the carbonylation process, e.g., methyl acetate, methyl iodide and catalyst, including low boiling components recovered in the product separation and recovery zone, are fed to tank 30 via conduit 26. The contents of tank 30 are fed to carbonylation reactor 10 via conduits 2 and 6. Methanol may be fed to line 2 via conduit 4 to convert recycle acetic anhydride to methyl acetate and acetic acid. Carbon monoxide, optionally containing a minor amount of hydrogen, is fed to carbonylation reactor 10 by means of conduit 8 and gas sparger 9.

Accompanying FIG. 2 is a variation of the process depicted by FIG. 1 and described above. A liquid carbonylation product effluent is removed from carbonylation reactor 10 by means of conduit 12, passed through pressure reduction valve 13 and fed to evaporation vessel 20 by conduit 14. About 30 to 45 weight percent of the product fed to evaporator 20 is vaporized adiabatically and the vapor is removed via conduit 22. The liquid residue is removed from evaporator 20 and transferred to second evaporation vessel 40 by conduits 24 and 26. Methanol, water, or a mixture thereof is fed via conduit 28 to conduit 24 wherein the methanol and/or water reacts exothermically with acetic anhydride to produce acetic acid or a mixture of acetic acid and methyl acetate. The heat generated by the methanol and/or water addition assists in the vaporization of about 10 to 50 weight percent of the material fed to evaporator 40 via conduit 26. The vapor is removed from evaporator 40 via conduit 42 and combined with the vapor of conduit 22 in conduit 44 which is fed to a product separation and recovery zone (not shown). Liquid residue comprising acetic acid, optionally acetic anhydride and catalyst or catalyst components is removed from evaporator 40 by conduit 44 and fed to catalyst recycle tank 30. Materials required for the carbonylation process are fed to tank 30 via conduit 46. The contents of tank 30 are fed to carbonylation reactor 10 via conduits 2 and 6. Methanol may be fed to line 2 via conduit 4 to convert recycle acetic anhydride to methyl acetate and acetic acid. Carbon monoxide, optionally containing a minor amount of hydrogen, is fed to carbonylation reactor 10 by means of conduit 8 and gas sparger 9.

Accompanying FIG. 3 is a process flow diagram depicting a variation of the processes represented by FIGS. 1 and 2 and described above. A liquid carbonylation product effluent is removed from carbonylation reactor 10 by means of conduit 12, passed through pressure reduction valve 13 and fed to evaporation vessel 20 by conduit 14. About 30 to 55 weight percent of the crude carbonylation product fed to evaporator 20 is vaporized adiabatically and the vapor is removed via conduit 22. Liquid residue is removed from evaporator 20 and transferred to second evaporation vessel 40 by conduits 24 and 26. Methanol, water, or a mixture thereof is fed via conduit 28 to conduit 24 wherein the methanol and/or water reacts exothermically with acetic anhydride to produce acetic acid or a mixture of acetic acid and methyl acetate. The heat generated by the methanol and/or water addition/reaction assists in the vaporization of about 10 to 50 weight percent of the material fed to evaporator 40 via conduit 26. Vapor is removed from evaporator 40 via conduit 42 and combined in conduit 44 with the vapor from conduit 22. Liquid residue comprising acetic acid, optionally acetic anhydride and catalyst or catalyst components is removed from evaporator 40 by conduit 46 and fed via heat exchanger 47 and conduit 48 to third evaporation vessel 50. The heat provided by heat exchanger 47 causes vaporization of about 20 to 60 weight percent of the material fed to evaporator 50 via conduit 48. Vapor is removed from evaporator 50 via conduit 52 and combined in conduit 54 with the vapor from conduit 44. The combined vapor streams are fed to a product separation and recovery zone (not shown). Liquid residue comprising acetic acid, optionally acetic anhydride and catalyst or catalyst components is removed from evaporator 50 by conduit 56 and fed to catalyst recycle tank 30. Materials required for the carbonylation process are fed to tank 30 via conduit 58. The contents of tank 30 are fed to carbonylation reactor 10 via conduits 2 and 6. Methanol may be fed to line 2 via conduit 4 to convert recycle acetic anhydride to methyl acetate and acetic acid. Carbon monoxide, optionally containing a minor amount of hydrogen, is fed to carbonylation reactor 10 by means of conduit 8 and gas sparger 9.

Our invention also provides a process for purifying a carbonylation product mixture, comprising: (i) producing a carbonylation product mixture comprising acetic anhydride, methyl acetate, methyl iodide, and catalyst components; (ii) feeding the carbonylation product mixture to an evaporation zone; (iii) contacting the carbonylation product mixture with water, methanol, or a mixture thereof to convert at least a portion of the acetic anhydride to acetic acid, methyl acetate, or a mixture thereof and heat; and (iv) using the heat of step (iii) to vaporize at least a portion of the carbonylation product mixture; and (v) recovering from the evaporation zone a vapor product effluent comprising methyl iodide and acetic acid, methyl acetate, or a mixture thereof, and a liquid product effluent comprising acetic acid, catalyst components, and, optionally, acetic anhydride. It is understood that the process includes the various embodiments for the carbonylation product mixture and components, catalyst, promoters, evaporators, various process conditions and unit operations, temperature, pressures, feedstocks, and process streams described hereinabove and in any combination.

EXAMPLE

Our novel process is further illustrated by the following example wherein all parts and percentages are by weight unless specified otherwise. The example utilizes the separation system shown in FIG. 3 and a liquid carbonylation product effluent obtained from a reaction zone similar to the production system described in U.S. Pat. No. 5,922,911. A liquid carbonylation product effluent is removed via conduit 12 from the carbonylation zone at a temperature of 195° C. and a pressure of 22 barg at a rate of 100 parts per hour. The pressure of this product stream is reduced to 3 barg by means of pressure reduction valve 13 and the stream is fed via conduit 14 to evaporator 20 wherein about 29% of the feed stream is vaporized and the vapor is removed from evaporator 20 via conduit 22 at a rate of 29 parts per hour. Liquid residue is removed from evaporator 20 at a rate of 71 parts per hour and fed to evaporator 40 via conduits 24 and 26. Methanol is fed to conduit 24 via conduit 28 at a rate of 3.5 parts per hour. A vapor is removed from evaporator 40 via conduit 42 at a rate of 17 parts per hour. Liquid residue is removed from evaporator 40 at a rate of 58 parts per hour and is fed first to heat exchanger 47 and then to evaporator 50 via conduit 48. Sufficient heat is provided by heat exchanger 47 to cause vaporization within evaporator 50 and removal of vapor via conduit 52 at a rate of 37 parts per hour. Liquid residue is removed from evaporator 50 at a rate of 21 parts per hour and is transferred to catalyst recycle tank 30. The total amount of material comprising the liquid carbonylation and 54 in the vaporization zone averages about 80%.

The approximate average composition (weight percent) of some of the streams referred to in the example are shown in the Table wherein $Ac_2O$ is acetic anhydride, HOAc is acetic acid, MeOAc is methyl acetate, MeI is methyl product effluent plus the added methanol vaporized and collected by conduits 22, 42, 44, 52 iodide and Other is a mixture of catalyst and by-products such as acetone, ethylidene diacetate, acetyl iodide and tars.

TABLE

| Conduit No. | $Ac_2O$ | HOAc | MeOAc | MeI | Other |
|---|---|---|---|---|---|
| 12 | 24 | 36 | 20 | 11 | 9 |
| 22 | 12 | 25 | 34 | 24 | 5 |
| 26 | 3 | 55 | 26 | 4 | 12 |
| 42 | 2 | 37 | 48 | 10 | 3 |
| 48 | 15 | 50 | 18 | 4 | 13 |
| 52 | 1 | 38 | 48 | 10 | 1 |
| 56 | 19 | 46 | 6 | 1 | 28 |

The invention has been described in detail with particular reference to preferred embodiments thereof, but it will be understood that variations and modifications can be effected within the spirit and scope of the invention.

We claim:
1. A process for the production of acetic acid or a mixture of acetic acid and acetic anhydride in the liquid phase, comprising:
   (1) continuously feeding to a reaction zone (i) a feedstock compound selected from methyl acetate, dimethyl ether or a mixture thereof, (ii) methyl iodide, (iii) dissolved catalyst components, (iv) acetic acid, and (v) carbon monoxide, wherein the feedstock compound is converted to acetic anhydride at a temperature of about 100 to 300° C. and a total pressure of about 21 to 276 bar gauge to produce a liquid carbonylation product mixture comprising (i) a feedstock compound selected from methyl acetate, dimethyl ether or a mixture thereof, (ii) methyl iodide, (iii) dissolved catalyst components, (iv) acetic acid, (v) dissolved carbon monoxide and (vi) acetic anhydride product;
   (2) feeding liquid carbonylation product effluent from the reaction zone to an evaporation zone comprising at least one evaporation vessel wherein the total pressure is about 1 to 10 barg;
   (3) removing from the evaporation zone a vapor product effluent constituting about 30 to 90 weight percent of the liquid carbonylation product fed to the evaporation zone and comprising the feedstock compound; methyl iodide, acetic acid, and optionally acetic anhydride; and
   (4) removing from the evaporation zone a liquid product effluent constituting about 10 to 70 weight percent of the liquid reaction mixture fed to the evaporation zone and comprising acetic acid, optionally acetic anhydride and dissolved catalyst components;
   wherein methanol, water, or a mixture thereof is combined with liquid carbonylation product effluent (i) fed to the evaporation zone and/or (ii) within the evaporation zone and reacts exothermically with acetic anhydride to produce acetic acid or a mixture of acetic acid and methyl acetate and the heat of the methanol/acetic anhydride and/or water/acetic anhydride reaction increases the weight percent of vapor product removed from the evaporation zone.

2. Process according to claim 1 wherein the total amount of methanol and/or water combined with the liquid carbonylation product effluent fed to the evaporation zone is about 0.1 to 1 mole of methanol per mole of acetic anhydride present in the product stream.

3. Process according to claim 1 wherein the total amount of methanol and/or water combined with the liquid carbonylation product effluent fed to the evaporation zone is about 0.3 to 0.6 mole of methanol per mole of acetic anhydride present in the product stream.

4. Process according to claim 1 wherein methanol is combined with the liquid carbonylation product effluent fed to the evaporation zone and the resulting mixture is fed to an evaporation vessel; a vapor product effluent constituting about 30 to 80 weight percent of the liquid carbonylation product fed to the evaporation vessel and comprising the feedstock compound; methyl iodide, acetic acid, and acetic anhydride is removed from the evaporation vessel; the vapor product is fed to a refining system wherein low boilers are recovered and acetic acid and acetic anhydride are separated and recovered; and a liquid product effluent comprising acetic acid, acetic an hydride and dissolved catalyst components is recycled to the reaction zone.

5. Process according to claim 1 wherein:
   the liquid carbonylation product effluent is fed to a first evaporation vessel to produce a vapor product effluent comprising the feedstock compound; methyl iodide, acetic acid, and acetic anhydride and a liquid product effluent comprising acetic acid, acetic anhydride and dissolved catalyst components;
   methanol is combined with liquid product effluent from the first evaporation vessel and the resulting mixture is fed to a second evaporation vessel to produce a vapor product effluent comprising the feed stock compound; methyl iodide, acetic acid, and acetic anhydride and a liquid product effluent comprising acetic acid, acetic anhydride and dissolved catalyst components;
   vapor product effluent from the first and second evaporation vessels constituting about 30 to 80 weight percent of the liquid carbonylation product fed to the evaporation zone and comprising the feedstock compound; methyl iodide, acetic acid, and acetic anhydride removed from the second evaporation vessel is fed to a refining system wherein low boilers are recovered and acetic acid and acetic anhydride are separated and recovered; and
   liquid product effluent comprising acetic acid, acetic anhydride and dissolved catalyst components from the second evaporation vessel is recycled to the reaction zone.

6. Process according to claim 1 wherein:
   liquid carbonylation product effluent is fed to a first evaporation vessel to produce a vapor product effluent comprising the feed stock compound, methyl iodide, acetic acid, and acetic anhydride and a liquid product effluent comprising acetic acid, acetic anhydride and dissolved catalyst components;
   methanol is combined with liquid product effluent from the first evaporation vessel and the resulting mixture is fed to a second evaporation vessel to produce a vapor product effluent comprising the feedstock compound; methyl iodide, acetic acid, and acetic anhydride and a liquid product effluent comprising acetic acid, acetic anhydride and dissolved catalyst components;

liquid product effluent from the second evaporation vessel is heated and fed to a third evaporation vessel to produce a vapor product effluent comprising the feedstock compound; methyl iodide, acetic acid, and acetic anhydride and a liquid product effluent comprising acetic acid, acetic anhydride and dissolved catalyst components;

vapor product effluent from the first, second and third evaporation vessels constituting about 30 to 90 weight percent of the liquid carbonylation product fed to the evaporation zone and comprising the feedstock compound; methyl iodide, acetic acid, and acetic anhydride removed from the third evaporation vessel is fed to a refining system wherein low boilers are recovered and acetic acid and acetic anhydride are separated and recovered; and liquid product effluent comprising acetic acid, acetic anhydride and dissolved catalyst components from the second evaporation vessel is recycled to the reaction zone.

7. Process according to claim 1 wherein:

water is combined with the liquid carbonylation product effluent fed to the evaporation zone and the resulting mixture is fed to an evaporation vessel;

a vapor product effluent constituting about 30 to 80 weight percent of the liquid carbonylation product fed to the evaporation vessel and comprising the feedstock compound; methyl iodide, acetic acid, and optionally acetic anhydride is removed from the evaporation vessel;

the vapor product effluent is fed to a refining system wherein low boilers are recovered and acetic acid and optionally acetic anhydride are separated and recovered; and a liquid product effluent comprising acetic acid, optionally acetic anhydride and dissolved catalyst components is recycled to the reaction zone.

8. Process according to claim 1 wherein:

the liquid carbonylation product effluent is fed to a first evaporation vessel to produce a vapor product effluent comprising the feedstock compound; methyl iodide, acetic acid, and acetic anhydride and a liquid product effluent comprising acetic acid, optionally acetic anhydride and dissolved catalyst components;

water is combined with liquid product effluent from the first evaporation vessel and the resulting mixture is fed to a second evaporation vessel to produce a vapor product effluent comprising the feedstock compound; methyl iodide, acetic acid, and optionally acetic anhydride and a liquid product effluent comprising acetic acid, optionally acetic anhydride and dissolved catalyst components;

vapor product effluent from the first and second evaporation vessels constituting about 30 to 80 weight percent of the liquid carbonylation product fed to the evaporation zone and comprising the feedstock compound; methyl iodide, acetic acid, and optionally acetic anhydride removed from the second evaporation vessel is fed to a refining system wherein low boilers are recovered and acetic acid and optionally acetic anhydride are separated and recovered; and liquid product effluent comprising acetic acid, optionally acetic anhydride and dissolved catalyst components from the second evaporation vessel is recycled to the reaction zone.

9. Process according to claim 1 wherein:

liquid carbonylation product effluent is fed to a first evaporation vessel to produce a vapor product effluent comprising the feedstock compound; methyl iodide, acetic acid, and acetic anhydride and a liquid product effluent comprising acetic acid, acetic anhydride and dissolved catalyst components;

water is combined with liquid product effluent from the first evaporation vessel and the resulting mixture is fed to a second evaporation vessel to produce a vapor product effluent comprising the feedstock compound; methyl iodide, acetic acid, and optionally acetic anhydride and a liquid product effluent comprising acetic acid, optionally acetic anhydride and dissolved catalyst components;

liquid product effluent from the second evaporation vessel is heated and fed to a third evaporation vessel to produce a vapor product effluent comprising the feedstock compound; methyl iodide, acetic acid, and optionally acetic anhydride and a liquid product effluent comprising acetic acid, optionally acetic anhydride and dissolved catalyst components;

vapor product effluent from the first, second and third evaporation vessels constituting about 30 to 90 weight percent of the liquid carbonylation product fed to the evaporation zone and comprising the feedstock compound; methyl iodide, acetic acid, and optionally acetic anhydride removed from the third evaporation vessel is fed to a refining system wherein low boilers are recovered and acetic acid and acetic anhydride are separated and recovered; and liquid product effluent comprising acetic acid, optionally acetic anhydride and dissolved catalyst components from the second evaporation vessel is recycled to the reaction zone.

10. A process for the coproduction of acetic anhydride and acetic acid in the liquid phase under substantially anhydrous conditions comprising:

(1) continuously feeding to a reaction zone (i) a feedstock compound selected from methyl acetate, dimethyl ether or a mixture thereof, (ii) methyl iodide, (iii) dissolved catalyst components selected from rhodium, iridium and compounds thereof, (iv) acetic acid, and (v) carbon monoxide, wherein the feedstock compound is converted to acetic anhydride at a temperature of about 175 to 220° C. and a total pressure of about 37 to 106 bar gauge to produce a liquid carbonylation product mixture comprising (i) a feedstock compound selected from methyl acetate, dimethyl ether or a mixture thereof, (ii) methyl iodide, (iii) dissolved catalyst components, (iv) acetic acid, (v) dissolved carbon monoxide and (vi) acetic anhydride product;

(2) feeding liquid carbonylation product effluent from the reaction zone to an evaporation zone comprising at least one evaporation vessel wherein the total pressure is about 1 to 10 barg;

(3) removing from the evaporation zone a vapor product effluent constituting about 30 to 90 weight percent of the liquid carbonylation product fed to the evaporation zone and comprising the feedstock compound; methyl iodide, acetic acid, and acetic anhydride; and (4) removing from the evaporation zone a liquid product effluent constituting about 10 to 70 weight percent of the liquid reaction mixture fed to the evaporation zone and comprising acetic acid, acetic anhydride and dissolved catalyst components;

wherein methanol is combined with liquid carbonylation product effluent (i) fed to the evaporation zone and/or (ii) within the evaporation zone and reacts exothermically with acetic anhydride to produce acetic acid and methyl acetate and the heat of the methanol/acetic anhydride reaction increases the weight percent of vapor product removed from the evaporation zone and wherein the total amount of methanol combined with the liquid carbonylation product stream fed to the evaporation zone is about 0.3 to 0.6 mole of methanol per mole of acetic anhydride present in the product stream.

11. A process for the production of acetic acid or a mixture of acetic acid and acetic anhydride in the liquid phase comprising:
(1) continuously feeding to a reaction zone (i) a feedstock compound selected from methyl acetate, dimethyl ether or a mixture thereof, (ii) methyl iodide, (iii) dissolved catalyst components selected from rhodium, iridium and compounds thereof, (iv) acetic acid, and (v) carbon monoxide, wherein the feedstock compound is converted to acetic anhydride at a temperature of about 175 to 220° C. and a total pressure of about 37 to 106 bar gauge to produce a liquid carbonylation product mixture comprising (i) a feedstock compound selected from methyl acetate, dimethyl ether or a mixture thereof, (ii) methyl iodide, (iii) dissolved catalyst components, (iv) acetic acid, (v) dissolved carbon monoxide and (vi) acetic anhydride product;
(2) feeding liquid carbonylation product effluent from the reaction zone to an evaporation zone comprising at least one evaporation vessel wherein the pressure (total) is about 1 to 10 barg;
(3) removing from the evaporation zone a vapor product effluent constituting about 30 to 90 weight percent of the liquid carbonylation product fed to the evaporation zone and comprising the feedstock compound; methyl iodide, acetic acid, and optionally acetic anhydride; and
(4) removing from the evaporation zone a liquid product effluent constituting about 10 to 70 weight percent of the liquid reaction mixture fed to the evaporation zone and comprising acetic acid, optionally acetic anhydride and dissolved catalyst components;
wherein water is combined with liquid carbonylation product effluent (i) fed to the evaporation zone and/or (ii) within the evaporation zone and reacts exothermically with acetic anhydride to produce acetic acid and the heat of the water/acetic an hydride reaction increases the weight percent of vapor product removed from the evaporation zone and wherein the total amount of water combined with the liquid carbonylation product stream fed to the evaporation zone is about 0.1 to 1.0 mole of water per mole of acetic anhydride present in the product stream.

12. The process according to claim 1 wherein the liquid carbonylation product effluent fed to the evaporation zone comprises about 15 to 50 weight percent acetic anhydride.

13. The process according to claim 10 wherein the liquid carbonylation product effluent fed to the evaporation zone comprises about 15 to 50 weight percent acetic anhydride.

14. The process according to claim 11 wherein the liquid carbonylation product effluent fed to the evaporation zone comprises about 15 to 50 weight percent acetic anhydride.

* * * * *